(12) United States Patent
Braido et al.

(10) Patent No.: US 10,433,791 B2
(45) Date of Patent: Oct. 8, 2019

(54) PROSTHETIC HEART DEVICES HAVING DIAGNOSTIC CAPABILITIES

(71) Applicant: St. Jude Medical, Cardiology Division, Inc., St. Paul, MN (US)

(72) Inventors: Peter N. Braido, Wyoming, MN (US); Mina S. Fahim, Shoreview, MN (US); Loell Boyce Moon, Ham Lake, MN (US); Paul E. Ashworth, Wyoming, MN (US); Neelakantan Saikrishnan, Plymouth, MN (US); Steven Frederick Anderl, Forest Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 20 days.

(21) Appl. No.: 14/825,407

(22) Filed: Aug. 13, 2015

(65) Prior Publication Data

US 2016/0045316 A1 Feb. 18, 2016

Related U.S. Application Data

(60) Provisional application No. 62/038,512, filed on Aug. 18, 2014.

(51) Int. Cl.
*A61F 2/24* (2006.01)
*A61B 5/00* (2006.01)
(Continued)

(52) U.S. Cl.
CPC .............. *A61B 5/6862* (2013.01); *A61B 5/02* (2013.01); *A61B 5/026* (2013.01); *A61B 5/0215* (2013.01);
(Continued)

(58) Field of Classification Search
CPC ...... A61F 2/91; A61F 2230/0069; A61F 2/07; A61F 2220/0016; A61F 2250/0096;
(Continued)

(56) References Cited

U.S. PATENT DOCUMENTS

| 4,275,469 A | 6/1981 | Gabbay |
| 4,491,986 A | 1/1985 | Gabbay |

(Continued)

FOREIGN PATENT DOCUMENTS

| DE | 19857887 B4 | 5/2005 |
| DE | 10121210 B4 | 11/2005 |

(Continued)

OTHER PUBLICATIONS

International Search Report and Written Opinion for Application No. PCT/US2015/044969 dated Dec. 11, 2015.

(Continued)

*Primary Examiner* — Ann Schillinger
(74) *Attorney, Agent, or Firm* — Lerner, David, Littenberg, Krumholz & Mentlik, LLP

(57) ABSTRACT

A prosthetic device for implanting in a patient's heart includes (i) a therapeutic device capable of restoring function to a native heart valve; and (ii) at least one sensor including a body, an inductor coil disposed within the body, and a capacitor in communication with the inductor coil, the at least one sensor being coupled to the therapeutic device, and being configured to monitor proper function of the therapeutic device within the patient's heart.

8 Claims, 11 Drawing Sheets

(51) Int. Cl.
*A61F 2/844* (2013.01)
*A61B 5/0215* (2006.01)
*A61B 5/02* (2006.01)
*A61B 5/026* (2006.01)
*A61B 17/00* (2006.01)
*A61B 17/12* (2006.01)

(52) U.S. Cl.
CPC ...... *A61B 5/02028* (2013.01); *A61B 5/02158* (2013.01); *A61B 5/6847* (2013.01); *A61B 17/0057* (2013.01); *A61B 17/12122* (2013.01); *A61F 2/24* (2013.01); *A61F 2/2412* (2013.01); *A61F 2/2418* (2013.01); *A61F 2/2445* (2013.01); *A61F 2/2448* (2013.01); *A61F 2/2466* (2013.01); *A61F 2/2472* (2013.01); *A61F 2/844* (2013.01); *A61B 2017/00022* (2013.01); *A61B 2017/00575* (2013.01); *A61B 2017/00632* (2013.01); *A61B 2562/0247* (2013.01); *A61F 2210/0066* (2013.01); *A61F 2220/0016* (2013.01); *A61F 2220/0075* (2013.01); *A61F 2230/0008* (2013.01); *A61F 2230/0034* (2013.01); *A61F 2230/0065* (2013.01); *A61F 2250/001* (2013.01); *A61F 2250/0002* (2013.01); *A61F 2250/0004* (2013.01); *A61F 2250/0063* (2013.01); *A61F 2250/0065* (2013.01)

(58) Field of Classification Search
CPC ........ A61F 2/06; A61F 2/2418; A61F 2/2445; A61F 2/82; A61F 2/95; A61F 2002/011; A61F 2002/018
See application file for complete search history.

(56) References Cited

U.S. PATENT DOCUMENTS

| | | |
|---|---|---|
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,487,760 A * | 1/1996 | Villafana ............ A61B 5/0031 607/119 |
| 5,847,760 A | 12/1998 | Elmaliach et al. |
| 5,855,601 A | 1/1999 | Bessler et al. |
| 5,935,163 A | 8/1999 | Gabbay |
| 5,961,549 A | 10/1999 | Nguyen et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,331,163 B1 | 12/2001 | Kaplan |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,869,444 B2 | 3/2005 | Gabbay |
| 6,893,460 B2 | 5/2005 | Spenser et al. |
| 6,908,481 B2 | 6/2005 | Cribier |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,374,573 B2 | 5/2008 | Gabbay |
| 7,381,218 B2 | 6/2008 | Schreck |
| 7,452,371 B2 | 11/2008 | Pavcnik et al. |
| 7,524,331 B2 | 4/2009 | Birdsall |
| RE40,816 E | 6/2009 | Taylor et al. |
| 7,585,321 B2 | 9/2009 | Cribier |
| 7,731,742 B2 | 6/2010 | Schlick et al. |
| 7,846,203 B2 | 12/2010 | Cribier |
| 7,846,204 B2 | 12/2010 | Letac et al. |
| 7,909,770 B2 | 3/2011 | Stern et al. |
| 7,914,569 B2 * | 3/2011 | Nguyen ............ A61F 2/2412 623/1.18 |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2002/0183628 A1 * | 12/2002 | Reich ............ A61B 5/02014 600/486 |
| 2003/0023303 A1 | 1/2003 | Palmaz et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2005/0096726 A1 | 5/2005 | Sequin et al. |
| 2005/0154321 A1 * | 7/2005 | Wolinsky ............ A61B 5/0031 600/486 |
| 2005/0165317 A1 * | 7/2005 | Turner ............ A61B 5/0031 600/486 |
| 2005/0256566 A1 | 11/2005 | Gabbay |
| 2006/0008497 A1 | 1/2006 | Gabbay |
| 2006/0122692 A1 | 6/2006 | Gilad et al. |
| 2006/0129216 A1 * | 6/2006 | Hastings ............ A61B 5/0215 607/115 |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0067027 A1 | 3/2007 | Moaddeb et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0129637 A1 | 6/2007 | Wolinsky et al. |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2010/0036484 A1 | 2/2010 | Hariton et al. |

(56) References Cited

U.S. PATENT DOCUMENTS

| | | |
|---|---|---|
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2011/0029072 A1 | 2/2011 | Gabbay |
| 2016/0045316 A1 | 2/2016 | Braido et al. |
| 2016/0256274 A1 | 9/2016 | Hayoz |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1050265 A2 | 11/2000 |
| EP | 1584306 A1 | 10/2005 |
| EP | 1598031 A2 | 11/2005 |
| EP | 1360942 B1 | 12/2005 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 03047468 A1 | 6/2003 |
| WO | 03103539 A1 | 12/2003 |
| WO | 2005055883 A1 | 6/2005 |
| WO | 06073626 A2 | 7/2006 |
| WO | 2008006003 A2 | 1/2008 |
| WO | 2008024180 A1 | 2/2008 |
| WO | 2008071817 A1 | 6/2008 |
| WO | 2009006602 A1 | 1/2009 |
| WO | 10008548 A2 | 1/2010 |
| WO | 10008549 A1 | 1/2010 |
| WO | 10096176 A1 | 8/2010 |
| WO | 10098857 A1 | 9/2010 |
| WO | 2012106344 A1 | 8/2012 |
| WO | 2015058808 A1 | 4/2015 |

OTHER PUBLICATIONS

International Search Report and Written Opinion for Application No. PCT/US2015/044962 dated Oct. 30, 2015.

Catheter-implanted prosthetic heart valves, Knudsen, L.L., et al., The International Journal of Artificial Organs, vol. 16, No. 5 1993, pp. 253-262.

Transluminal Aortic Valve Placement, Moazami, Nader, et al., ASAIO Journal, 1996; 42:M381-M385.

Transluminal Catheter Implanted Prosthetic Heart Valves, Andersen, Henning Rud, International Journal of Angiology 7:102-106 (1998).

Transluminal implantation of artificial heart valves, Andersen, H. R., et al., European Heart Journal (1992) 13, 704-708.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

* cited by examiner

PROSTHETIC HEART DEVICES HAVING DIAGNOSTIC CAPABILITIES

CROSS-REFERENCE TO RELATED APPLICATIONS

The present application claims the benefit of the filing date of U.S. Provisional Patent Application No. 62/038,512 filed Aug. 18, 2014, the disclosure of which is hereby incorporated herein by reference.

BACKGROUND OF THE INVENTION

The present invention relates to heart valve replacement and repair devices such as collapsible prosthetic heart valves. More particularly, the present invention relates to devices and methods for using prosthetic heart devices having diagnostic capabilities.

Diseased or damaged native heart valves may be repaired or replaced using prosthetic devices. In some instances, devices, such as annuloplasty rings, are used to repair and restore the function of a malfunctioning native heart valve. If repair is not possible, the function of native heart valves may be replaced by prosthetic devices, such as tissue valves (i.e., surgical valves). Such a replacement typically requires an open-heart surgical procedure.

In addition to these devices, prosthetic heart valves that are collapsible to a relatively small circumferential size can be delivered into a patient less invasively than surgical valves. For example, a collapsible valve may be delivered into a patient via a tube-like delivery apparatus such as a catheter, a trocar, a laparoscopic instrument, or the like. This collapsibility can avoid the need for more invasive procedures such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

It would be advantageous to monitor the function of prosthetic devices, including annuloplasty rings, surgical valves and transcatheter valves, before, during and after implantation to ensure proper function for short-term and long-term assessment. For example, calcification of the aortic valve may affect the performance and anchoring of transcatheter implants. Calcification may also be associated with leakage, such as paravalvular leakage around the exterior of a medical device or aortic regurgitation through the interior of a medical device.

There therefore is a need for improvements in the devices, systems, and methods for monitoring prosthetic heart devices before, during and after implantation. Specifically, there is a need for improvements in the devices, systems, and methods for accurately measuring parameters associated with proper prosthetic heart valve functionality. Among other advantages, the present disclosure may address one or more of these needs.

SUMMARY OF THE INVENTION

In some embodiments, a prosthetic device for implanting in a patient's heart includes a therapeutic device capable of restoring desired function to a native heart valve; and at least one sensor coupled to the therapeutic device and configured to monitor the function of the therapeutic device within the patient's heart, the sensor including a body, an induction coil disposed within the body and a capacitor in electrical communication with the inductor coil.

In some embodiments, a method for diagnosing the functioning of a heart includes (a) introducing a prosthetic device into the heart, the prosthetic device including (i) a therapeutic device capable of restoring function to a native heart valve, and (ii) at least one sensor including a body, an inductor coil disposed within the body, and a capacitor in communication with the inductor coil, the at least one sensor being coupled to the therapeutic device; (b) acquiring cardiac measurements via the at least one sensor; and (c) determining the functioning of the heart based on the cardiac measurements.

BRIEF DESCRIPTION OF THE DRAWINGS

Various embodiments of the present disclosure are disclosed herein with reference to the drawings, wherein.

Various embodiments of the present disclosure will now be described with reference to the appended drawings. It is to be appreciated that these drawings depict only some embodiments of the disclosure and are therefore not to be considered limiting of its scope.

DETAILED DESCRIPTION OF THE INVENTION

As used herein, the term "proximal," when used in connection with a prosthetic heart device, refers to the end of the heart device closest to the heart when the device is implanted in a patient, whereas the term "distal," when used in connection with a prosthetic heart device, refers to the end of the heart device farthest from the heart when the device is implanted in a patient.

Figure 1:
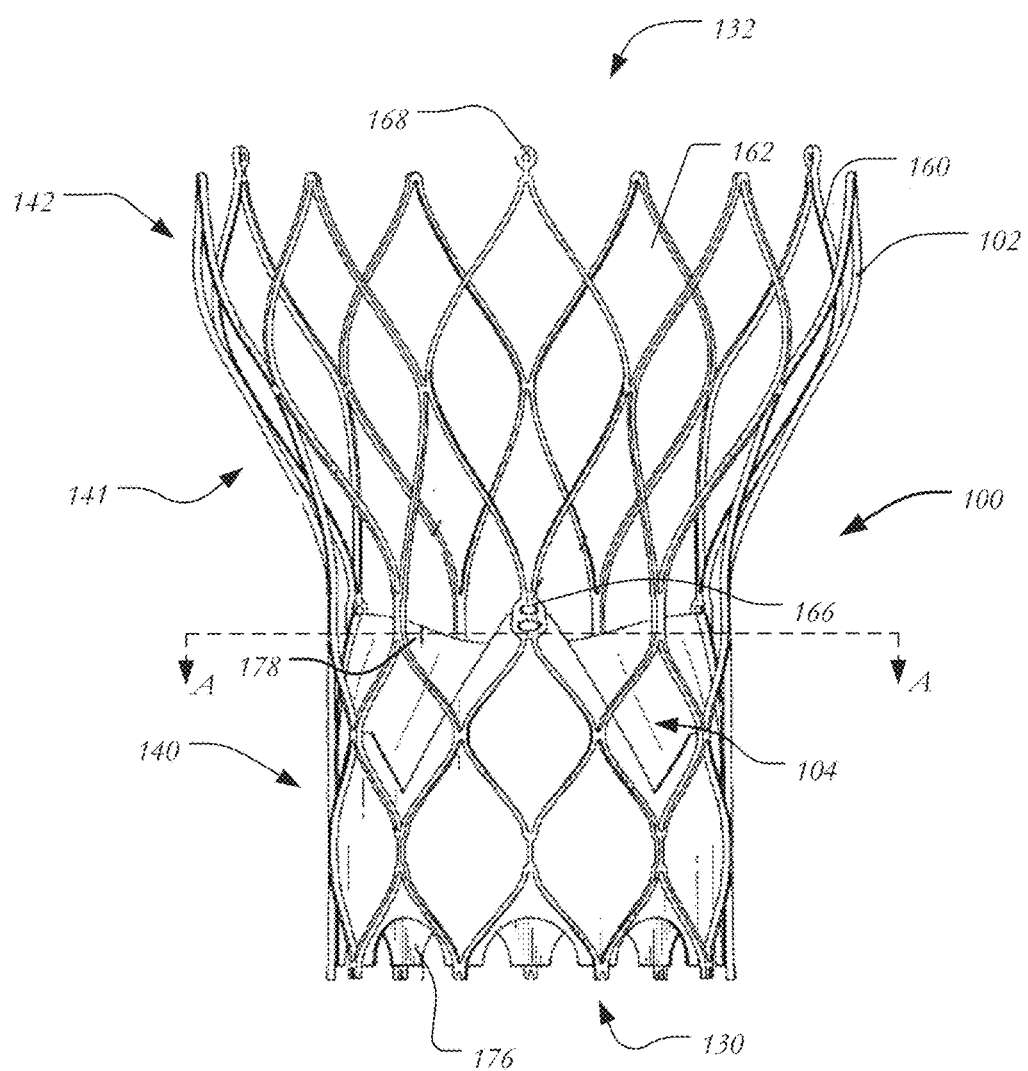
FIG. 1 is a partial side elevational view of a conventional prosthetic heart valve.

FIG. 1 shows one such collapsible stent-supported prosthetic heart valve 100 including a stent 102 and a valve assembly 104 as is known in the art. Prosthetic heart valve 100 is designed to replace a native tricuspid valve of a patient, such as a native aortic valve. It should be noted that while the embodiments discussed herein relate predominantly to prosthetic aortic valves having a stent with a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 (FIG. 1) includes expandable stent 102 which may be formed from biocompatible materials that are capable of self-expansion, such as, for example, shape memory alloys, such as the nickel-titanium alloy known as "Nitinol" or other suitable metals or polymers. Stent 102 extends from proximal or annulus end 130 to distal or aortic end 132, and includes annulus section 140 adjacent proximal end 130, transition section 141 and aortic section 142 adjacent distal end 132. Annulus section 140 may have a relatively small cross-section in the expanded configuration, while aortic section 142 may have a relatively large cross-section in the expanded configuration. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on a deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably secured to stent 102 in annulus section 140. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the sealing portions of the present disclosure may be used may have a greater or lesser number of leaflets.

Although cuff 176 is shown in FIG. 1 as being disposed on the lumenal or inner surface of annulus section 140, it is contemplated that cuff 176 may be disposed on the ablumenal or outer surface of annulus section 140 or may cover all or part of either or both of the lumenal and ablumenal surfaces. Both cuff 176 and leaflets 178 may be wholly or partly formed of any suitable biological material or polymer such as, for example, Polyethylene terephthalate (PET), ultra-high-molecular-weight polyethylene (UHMWPE), or polytetrafluoroethylene (PTFE).

Leaflets 178 may be attached along lower belly portions to cells 162 of stent 102, with the commissure between adjacent leaflets 178 attached to commissure features 166. As can be seen in FIG. 1, each commissure feature 166 may lay at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

In operation, the embodiment of the prosthetic heart valve described above may be used to replace a native heart valve, such as the aortic valve. The prosthetic heart valve may be delivered to the desired site (e.g., near a native aortic annulus) using any suitable delivery device. Typically, during delivery, the prosthetic heart valve is disposed inside the delivery device in the collapsed condition. The delivery device may be introduced into a patient using a transfemoral, transapical, transseptal or other percutaneous approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction. While the disclosures herein are predominantly described in terms of a tricuspid valve, the valve could be a bicuspid valve, such as the mitral valve, and the stent could have different shapes, such as a flared or conical annulus section, a less-bulbous aortic section, and the like, and a differently shaped transition section.

In certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency may benefit from the monitoring of an implanted prosthetic valve.

Figure 2:
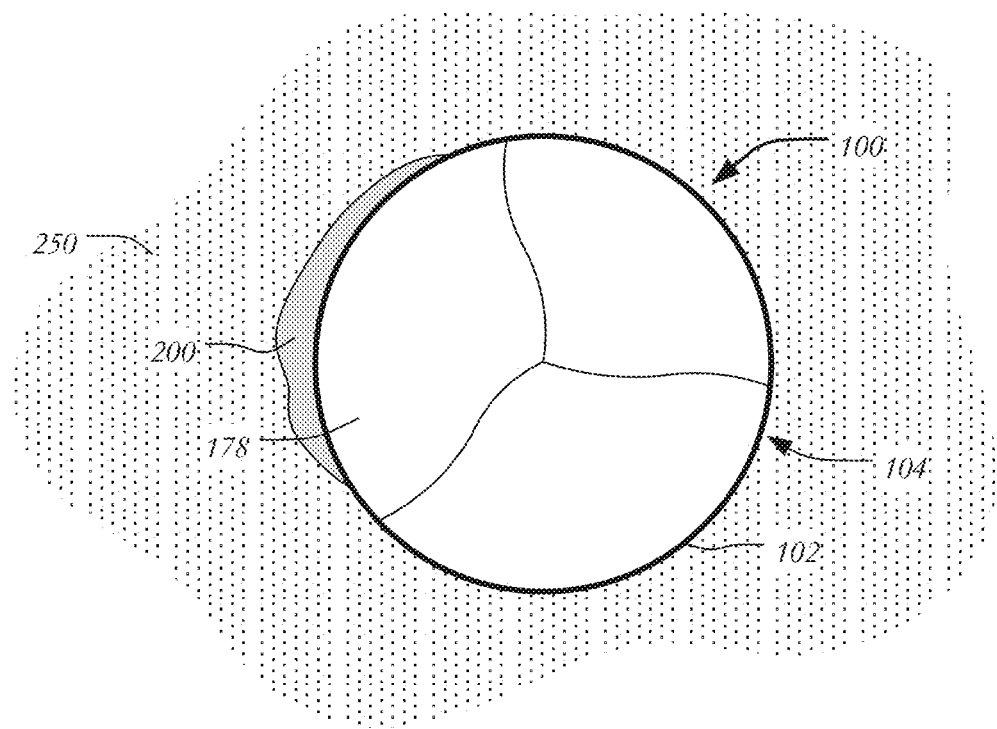
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, annulus section 140 of stent 102 has a substantially circular cross-section which is disposed within non-circular native valve annulus 250. At certain locations around the perimeter of heart valve 100, crescent-shaped gaps 200 form between the heart valve and native valve annulus 250. Blood flowing through these gaps and around leaflets 178 of valve assembly 104 can cause paravalvular leakage and other inefficiencies which reduce cardiac performance. Such improper fitment may result from suboptimal native valve annulus geometry due, for example, to calcification of native valve annulus 250 or to unresected native leaflets. Additionally, improper fitment may disrupt the proper coaptation of leaflets 178, leading to aortic regurgitation (e.g., leakage or backflow of blood between the leaflets). In order to address concerns regarding leakage, such as paravalvular leakage or aortic regurgitation, sensors may be utilized to monitor the performance of a prosthetic heart valve.

Figures 3A, 3B:
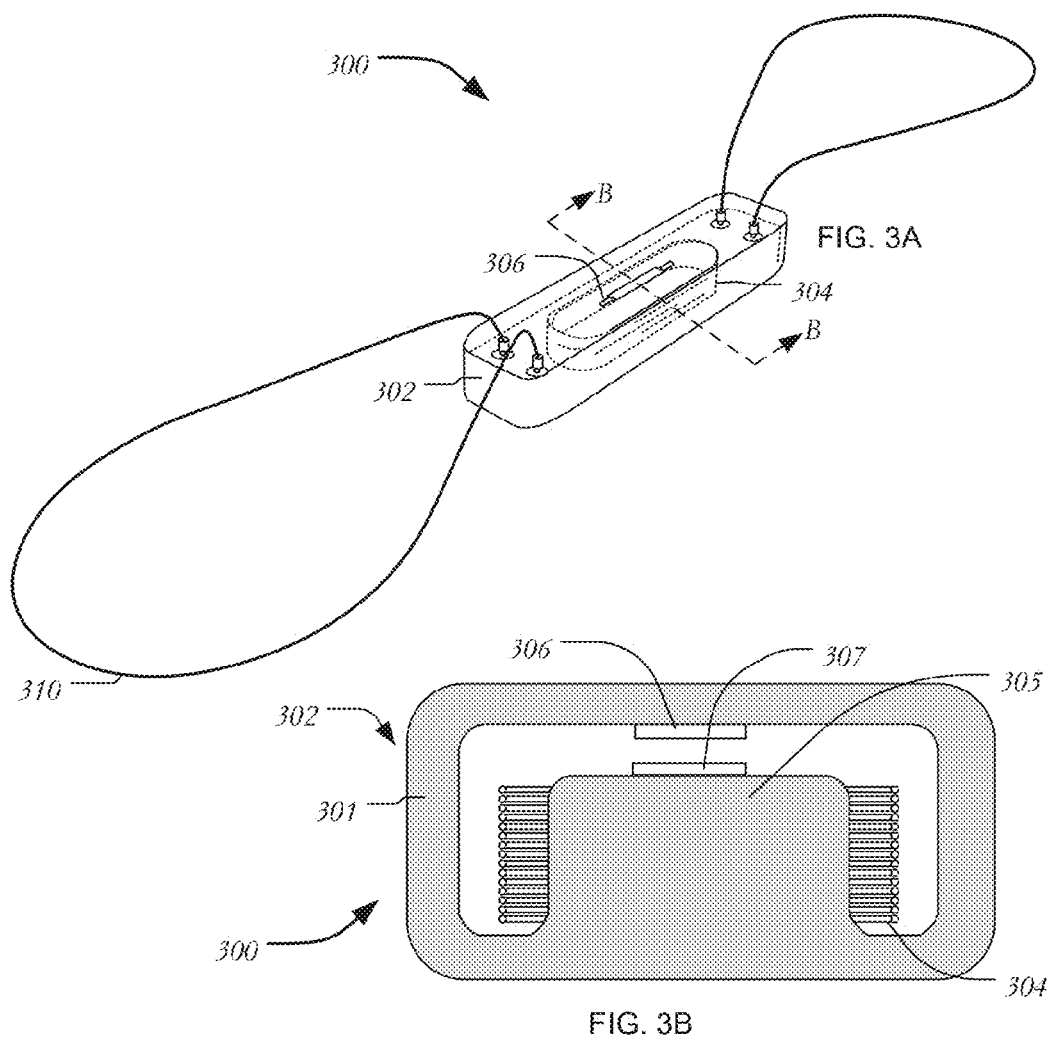
FIG. 3A is a perspective view of a microelectromechanical sensor according to one embodiment of the present disclosure.
FIG. 3B is a cross-sectional view taken along line B-B of FIG. 3A.

FIGS. 3A and 3B illustrate one example of a sensor for diagnostic usage. Sensor 300 generally includes body 302 formed of a generally hollow fused silica housing 301 with a silicone coating around the exterior of the housing. An elongated boss 305, also formed from fused silica, may project into the interior of housing 301 and may be formed integrally therewith. A plurality of electrically conductive windings may wrap around boss 305 to form an inductor coil 304. Capacitive plates 306 and 307 are separated by micrometer spacing, forming a variable capacitor. Capacitive plate 306 is sensitive to pressure and experiences nanometer scale deflections due to changes in blood pressure acting on the sensor 300. These nanometer scale deflections result in a change in the resonant frequency of circuit formed by the inductor coil 304 and pressure-sensitive capacitor formed by plated 306 and 307.

$$\text{Resonant Frequency} f_R = \frac{1}{2\pi\sqrt{L \times C(p)}},$$

where L is the inductance of inductor coil 304 and C(p) is the capacitance which varies with pressure. The entire assembly is hermetically sealed and does not come in contact with blood.

The sensor 300 can be electromagnetically coupled to a transmitting antenna (not shown). Consequently, a current is induced in the sensor 300, which oscillates at the resonant frequency of the circuit formed by the inductor coil 304 and pressure-sensitive capacitor formed by plated 306 and 307. This oscillation causes a change in the frequency spectrum of the transmitted signal. From this change, the bandwidth and resonant frequency of the particular sensor may be determined, from which the corresponding blood pressure can be calculated. Time-resolved blood pressure measurements can be correlated to flow using empirical relationships established in clinical literature.

As shown, sensor 300 includes optional nitinol loops 310 extending from each end of body 302 to stabilize the sensor at an implant location. It will be appreciated that sensor 300 includes no additional leads, batteries or active-fixation mechanisms. Sensor 300 is an externally modulated inductor-capacitor circuit, which is powered using radio frequency by the transmitting antenna. Additionally, sensor 300 may be relatively small (e.g., 3.5×2×15 mm). Other advantages of sensor 300 include its accuracy, durability, biocompatibility, and insensitivity to changes in body chemistry, biology or external pressure. Sensor 300 may optionally include one or more radiopaque components to aid in localization and imaging of the device.

Sensor 300 may be modified for various applications and tuned to selectively emphasize different parameters. For example, by varying the width of the windings of inductor coil 304, the number of turns and the gap between the upper and lower windings, the resonant frequency that the device operates at and the pressure sensitivity (i.e., the change in frequency as a result of membrane deflection) can be optimized for different applications. In general, the design allows for a very small gap between the windings (typically between about 3 and about 35 microns) that in turn provides a high degree of sensitivity while requiring only a minute movement of the capacitive plates 306 and 307 to sense pressure changes.

The thickness of sensor 300 may also be varied to alter mechanical properties. Thicker substrates for forming housing 301 are more durable for manufacturing. Thinner substrates allow for creation of thin pressure sensitive membranes for added sensitivity. In order to optimize both properties, sensor 300 may be manufactured using two complementary substrates of different thicknesses. For example, one side of sensor 300 may be constructed from a substrate having a thickness of about 200 microns. This provides the ability to develop and tune sensors based on the operational environment of the implanted sensor 300 In addition to changes to housing 301, other modifications may be made to the sensor depending on the application. For example, nitinol loops 310 may be removed and replaced with suture holes for attachment, and cantilevers or other structural members may be added. In some variations, sensors may be powered by kinetic motion, the body's heat pump, glucose, electron flow, Quantum Dot Energy, and similar techniques.

Sensors 300 may be used to measure one or more parameters including real time blood pressure, flow velocity (e.g., blood flow), apposition forces based on pressure changes due to interaction between two surfaces of the prosthetic valve, impingement forces, which are correlated to pressure changes caused by the interaction between a surface of the prosthetic device and native tissue, cardiac output, effective orifice area, pressure drop, and aortic regurgitation. Sensor 300 provides time-resolved pressure data which may be correlated to the parameters of interest based on empirical correlations that have been presented in literature. In some examples, sensors 300 may function similar to piezo-electric strain gauges to directly measure a parameter. Other parameters may be indirectly calculated. One specific method of using sensors 300 to measure aortic regurgitation will be described in greater detail below with references to FIGS. 5A, 5B, and 6.

Figure 4A:
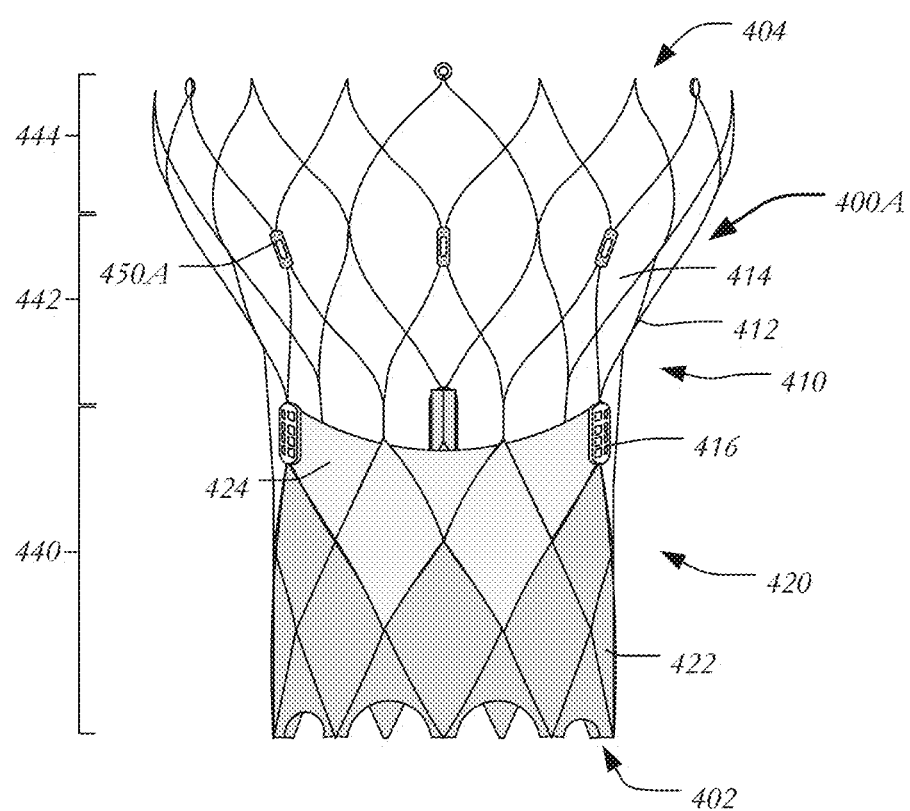
FIGS. 4A-F are side elevational views of several examples of a prosthetic heart devices having microelectromechanical sensors according to embodiments of the present disclosure.

FIG. 4A illustrates one example of a collapsible stent-supported prosthetic heart valve 400A having diagnostic capabilities as discussed above. Though heart valve 400A is illustrated as a collapsible aortic valve, it will be understood that the methods and techniques disclosed herein are equally applicable for other collapsible valves in the heart, such as, for example, mitral valves. Heart valve 400A generally includes stent 410 and valve assembly 420 disposed within stent 410.

Stent 410 may include a plurality of struts 412 forming a plurality of cells 414, struts 412 being formed of any of the materials described above with reference to FIG. 1. Additionally, stent 410 may include commissure features 416 for attaching leaflets and/or a cuff as will be described below. Stent 410 generally extends between proximal end 402 and distal end 404 and includes annulus section 440 adjacent proximal end 402, aortic section 444 adjacent distal end 404, and transition section 442 disposed between annulus action 440 and aortic section 442.

Valve assembly 420 may be disposed entirely within annulus section 440 as shown and may include a circumferential cuff 422 and a plurality of leaflets 424 formed of any of the materials described above for the cuff and leaflets of FIG. 1. Each leaflet 424 may be attached to cuff 422 and/or to selected struts 412 of stent 410, as well as to commissure features 416, while leaving a free edge for coapting with the free edges of other leaflets 424 to form a one-way valve.

As shown in FIG. 4A, one or more sensors 450A may be coupled to heart valve 400A. In this example, sensors 450A are disposed in transition section 442. More specifically, sensors 450A are disposed in the second full row of cells 414 from distal end 404 at the intersection of two annularly adjacent cells. Sensors 450A may be disposed at spaced positions around the circumference of stent 410, for example, on each intersection of annularly adjacent cells, at alternating intersections or in a regular or irregular pattern around the circumference.

Figure 4B:
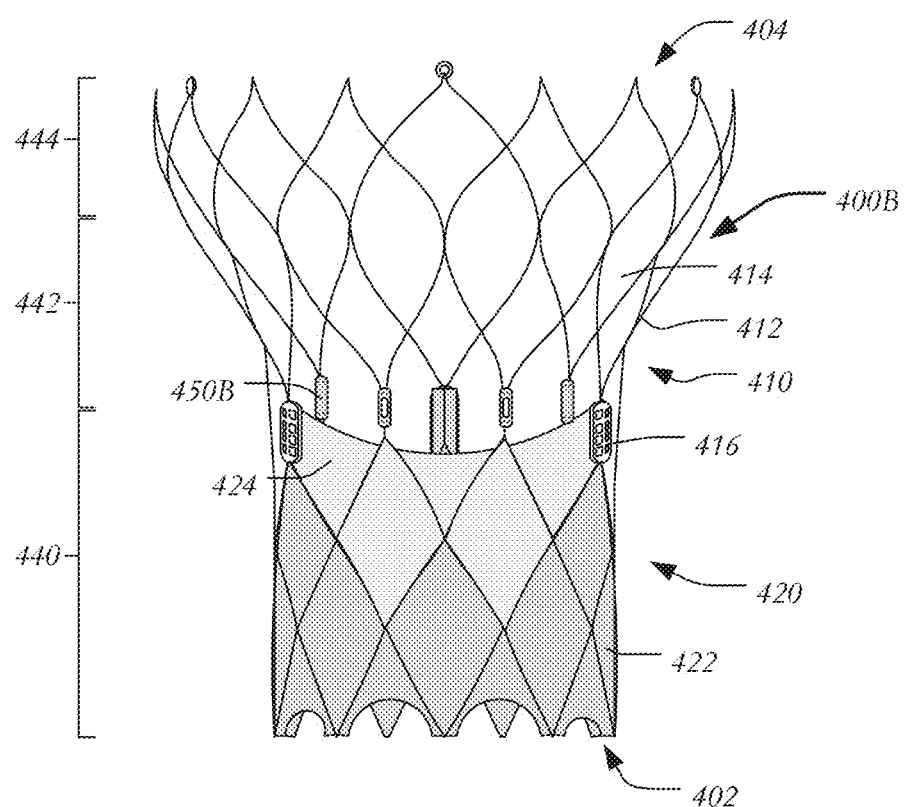

In a second example (FIG. 4B), heart valve 400B is similar to heart valve 400A and includes all of the components discussed above (e.g., stent 410, valve assembly 420, etc.). The main difference between heart valve 400B and 400A is in the placement of sensors 450B. As illustrated, sensors 450B are disposed in annulus section 440 at approximately the same longitudinal positions as commissure features 416. In one example, two sensors 450B are disposed between each adjacent pair of commissure features 416. As with the example of FIG. 4A, the number of sensors 450B may be varied as desired.

Figure 4C:
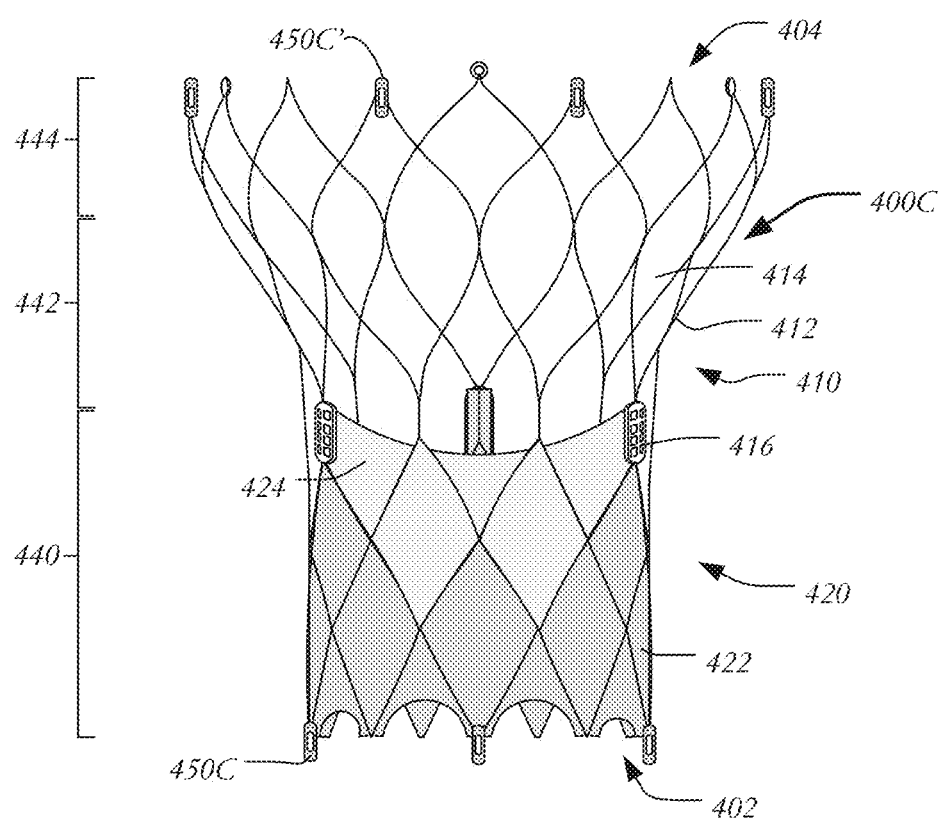

In a third example (FIG. 4C), heart valve 400C is similar to heart valves 400A and 400B and includes all of the components discussed above (e.g., stent 410, valve assembly 420, etc.), but differs in the placement of sensors. As illustrated, a first group of sensors 450C are disposed in annulus section 440 adjacent the proximal end 402 of stent 410, while a second group of sensors 450C' are disposed in aortic section 444 adjacent the distal end 404 of the stent. The first group of sensors 450C may be configured to monitor one or more parameters at the inflow end of heart valve 400C, while the second group of sensors 450C' may be configured to monitor one or more parameters at the outflow end of heart valve 400C. Any number of sensors may be used in either the first or second group of sensors. Additionally, it will be understood that in some variations, only one group of sensors (e.g., proximal sensors 450C only or distal sensors 450C' only) may be used, while eliminating the other group. In some variations, sensors may be placed at any joint, along a strut, attached to any cuff or leaflet surface, for example, by embedding the sensor within a leaflet and/or cuff if manufactured using techniques as three-dimensional printing. Sensors may also be cantilevered or strung across an inflow or outflow orifice. For example, at least one sensor may be disposed adjacent the inflow end and at least one sensor may be disposed adjacent the outflow end. Sensors may also be disposed on either the inner diameter, the outer diameter or a combination of both and may be sutured, glued, welded, or made integral with the stent, the leaflets and/or the cuff. Additionally, in certain variations, heart valves such as heart valve 400C may include paravalvular leakage features disposed about the circumference of stent 410. In such examples, sensors may be coupled to such paravalvular leakage features.

Figure 4D:
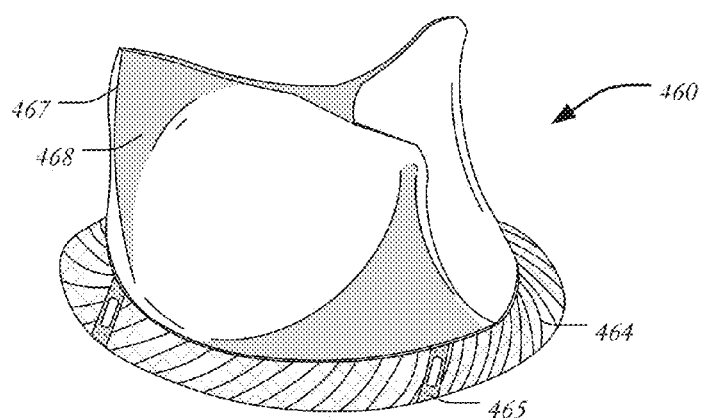

Though the previous three examples have illustrated sensors 450A-C disposed on collapsible heart valves, other applications of the sensors are possible. For example, FIG. 4D illustrates a stented surgical valve 460 that has been modified for diagnostic functionality. Valve 460 generally includes a fatigue-resistant metallic frame (not shown) (sometimes also referred to as a stent), disposed above a cuff 464 in the form of a ring. Pericardial tissue or other suitable material is supported by three posts 467 of the frame to form leaflets 468 of a one-way valve. In this example, sensors 465 are disposed on the periphery of cuff 465 and may be used to measure flow, such as, for example, aortic regurgitation. It will be understood that sensors 465 may be disposed on any other portion of valve 460, such as for example, on top of posts 467 or other portion of the frame, or directly onto leaflets 468. Additionally, though an aortic heart valve is shown, sensors 465 may be disposed on surgical valves configured for other applications (e.g., mitral valves).

Figure 4E:
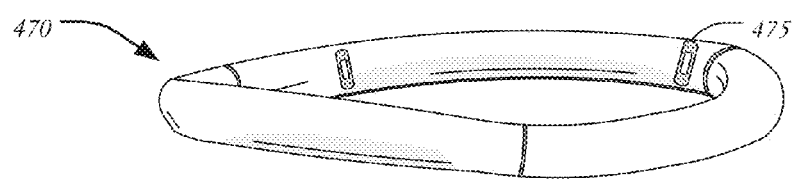

FIG. 4E illustrates another application, an annuloplasty ring 470 in this case, used for the repair of a native heart valve. Annuloplasty ring 470 is a surgical device used for the repair of leaking valves, such as for example, mitral valves. Due to various factors, the leaflets that normally seal a natural valve to retrograde flow may not coapt properly. Surgical repair typically involves the implantation of annuloplasty ring 470 to reshape the native valve annulus, which pulls the leaflets together to facilitate coaptation and aids to re-establish native valve function. Annuloplasty ring 470 may have one or more sensors 475 disposed on its inner or lumenal surface to monitor the function of the repaired native heart valve. It will be understood that sensors 475 may instead be formed on the ablumenal or outer surface of ring 410 and that the number of sensors 475 may be varied. In some variations, annuloplasty ring 470 may have an adjustable circumference, which may be varied, at least partially, based on measurements gathered by sensors 475.

Figure 4F:
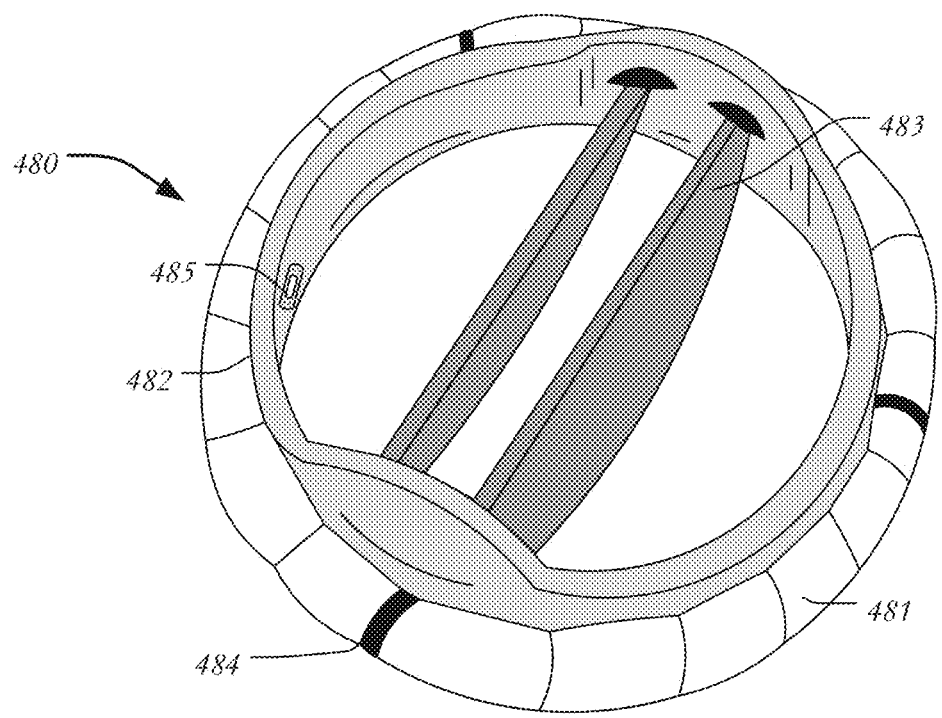

FIG. 4F illustrates yet another application, a mechanical valve 480, used for replacing the function of a native heart valve. Mechanical valve 480 may function similar to surgical valve 460 or heart valve 400 to replace function of, for example, an aortic valve or a mitral valve and generally includes cuff 481, support structure 482, two actuating disks 483 which function as leaflets to enable one-way flow. Cuff 481 may include a number of marker bands 484 for aid in localization. In the example shown, sensors 485 are disposed on the lumenal surface of support structure 482. It will be understood, however, that variations are possible in which sensors 485 are disposed on cuff 481, on ablumenal surfaces of either cuff 481 or support structure 482 or on disks 483 themselves.

Sensors may also be used with other therapeutic device including stents, embolic protection devices, plugs, etc. Additionally, though the embodiments of FIGS. 4A-E have illustrated sensors being disposed on therapeutic devices, it will be understood that the disclosure is not so limited. For example, sensors may be disposed either upstream (i.e., prior to the inflow end in the direction of blood flow) or downstream (i.e., after the outflow end in the direction of blood flow) of a therapeutic device (e.g., heart valve 400A) in order to obtain measurements at those sites. Thus one or more upstream and/or one or more downstream sensors may be used alone or in combination with sensor(s) disposed on the therapeutic devices.

As noted above, there are many applications for sensors 300. One such application uses sensors 300 in the direct assessment of the severity of aortic regurgitation. Aortic regurgitation negatively affects the prognosis after transcatheter aortic valve replacement, with dramatically increased morbidity and mortality in patients with more than mild regurgitation. Thus, techniques may be employed using sensors 300 to quantify the extent of regurgitation, if any.

One measure of regurgitation in aortic heart valves is the aortic regurgitation index, which may be defined as the ratio of the transvalvular gradient between diastolic blood pressure (RRdia) in the aorta and left-ventricular end-diastolic blood pressure (LVEDP) to systolic blood pressure (RRsys) in the aorta: $[(RRdia-LVEDP)/RRsys] \times 100$. The aortic regurgitation index has an inverse correlation to the severity of aortic regurgitation and allows a physician to differentiate between patients with mild, moderate, or severe aortic regurgitation. The aortic regurgitation index may also be independently used to predict the associated 1-year mortality risk for a given patient upon collection of data.

Figure 5A:
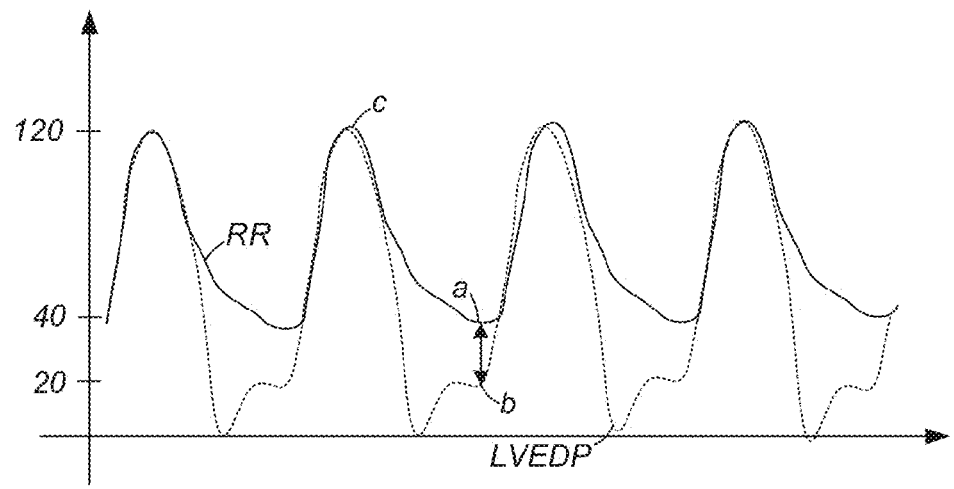
FIGS. 5A and 5B are graphs showing examples of hemodynamic assessments during transcatheter aortic valve replacement procedures.

FIG. 5A illustrates the aortic regurgitation index in a patient with moderate aortic regurgitation. Using the formula for the aortic regurgitation index defined above, the calculated result is 16.7, calculated as follows:

$$\frac{RRdia - LVEDP}{RRsys} \times 100 = \frac{a-b}{c} \times 100 = \frac{40-20}{120} \times 100 = 16.7$$

Figure 5B:
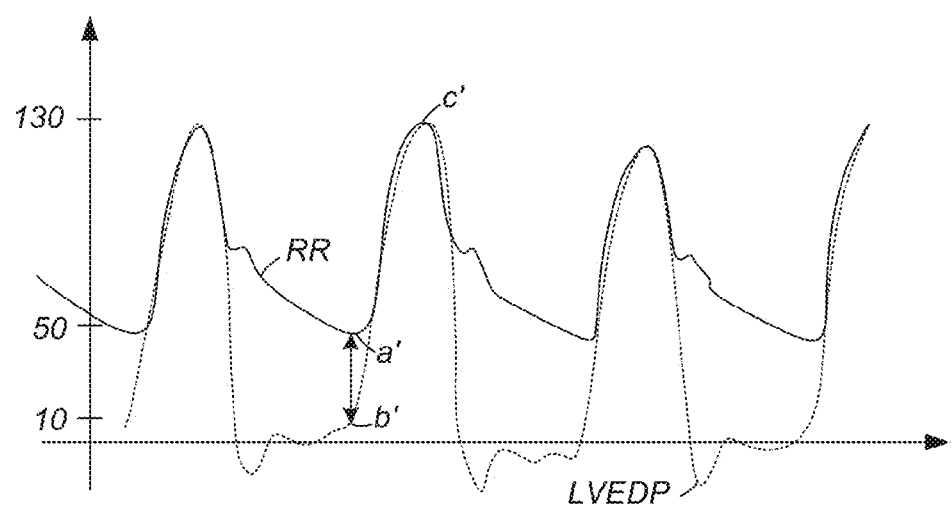

For a second patient, the aortic regurgitation index indicates a trivial amount of aortic regurgitation as shown in FIG. 5B and calculated below:

$$\frac{RRdia - LVEDP}{RRsys} \times 100 = \frac{a'-b'}{c'} \times 100 = \frac{50-10}{130} \times 100 = 30.8$$

When used in conjunction with prosthetic heart valves, sensors 300 may measure blood pressure to determine an aortic regurgitation index and thus reveal the severity of the regurgitation. Based on the calculated aortic regurgitation index, follow-up treatment may be advised. Additionally, sensors 300 may be used to decide when to fully deploy a partially deployed heart valve and the type of corrective measure necessary, if any.

Figure 6:
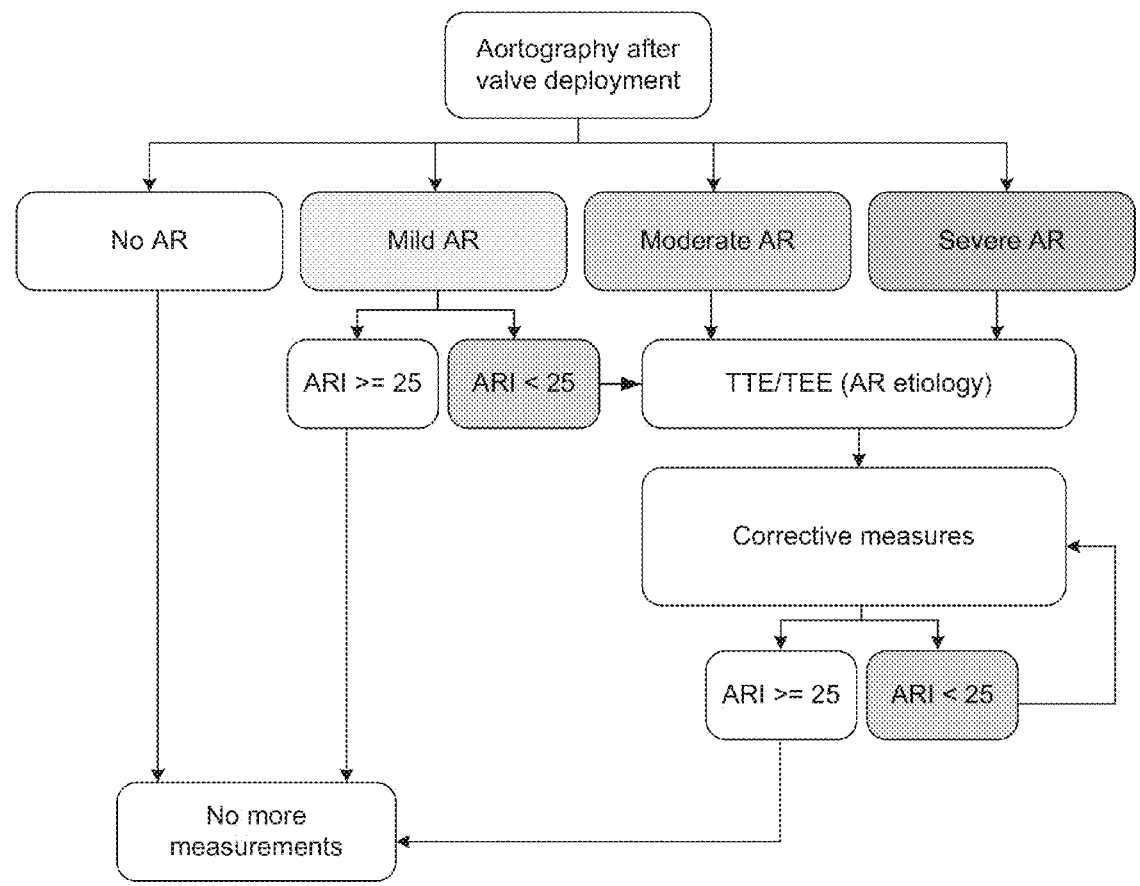
FIG. 6 is a flow chart showing one possible method of using the prosthetic heart valves of FIGS. 4A-C.

One example of a method using a prosthetic heart valve having sensors is shown in FIG. 6. In this method, a preliminary technique, such as but not limited to an aortography, may be performed after valve deployment in order to make a preliminary assessment of aortic regurgitation. This preliminary assessment may provide a rough classification of the regurgitation into four groups: no aortic regurgitation, mild aortic regurgitation, moderate aortic regurgitation and severe aortic regurgitation. If the preliminary technique shows no aortic regurgitation, then no measurements are taken and the procedure is determined to be a successful one (e.g., valve function is adequate). If the preliminary technique shows that mild aortic regurgitation is present, then sensors 300 may be used to quantify the amount of aortic regurgitation by calculating an aortic regurgitation index (ARI) as shown. An aortic regurgitation index greater than or equal to 25 may indicate that the aortic regurgitation is negligible, which results in no further measurement. If, however, the index is less than 25, then the aortic regurgitation may be classified as either moderate or severe. In either case, further diagnostic techniques, such as, for example, transesophageal echocardiography (TEE) or transthoracic echocardiography (TTE), may be performed to further assess the situation, followed by a corrective measure. The corrective measure may include any one or more of post-dilation techniques, snaring to re-adjust the position of the valve, valve-in-valve implantation (e.g., implanting an additional valve inside an already-implanted valve), balloon expansion, resheathing and redeploying techniques, deploying a valve of the same or different type, modified redeployment, or the additional of paravalvular leakage features, etc. Sensors 300 are then used to recalculate the aortic regurgitation index. If the aortic regurgitation index is greater than or equal to 25, then the corrective measure may be determined to be successful and no further measurements are taken. If, however, the aortic regurgitation index remains below 25, then further corrective measures may be necessary. This loop from corrective measure to aortic regurgitation index calculation may continue until satisfactory positioning and functioning of the prosthetic heart valve are obtained.

In the example above, the calculation of the aortic regurgitation index using sensors 300 is performed after implantation of the prosthetic heart valve to ensure proper functioning. In addition, sensors may be used to monitor an implanted prosthetic heart valve or repair device at any time, including before implantation of a therapeutic device or after discharge of the patient from the hospital. For example, sensors may be used to aid in implantation of a therapeutic device. In one example, sensors may be used to virtually reconstruct the geometry of the native valve annulus to predict potential paravalvular leakage of a heart valve with known dimensions. Such sensors may be used alone or in combination with a balloon expanded, or self-expanding diagnostic rings, holders, sizers, stents or balloons. For valve-in-valve procedures, sensors on an already implanted valve may be used to aid in docking a second valve within the implanted valve.

Figure 7:
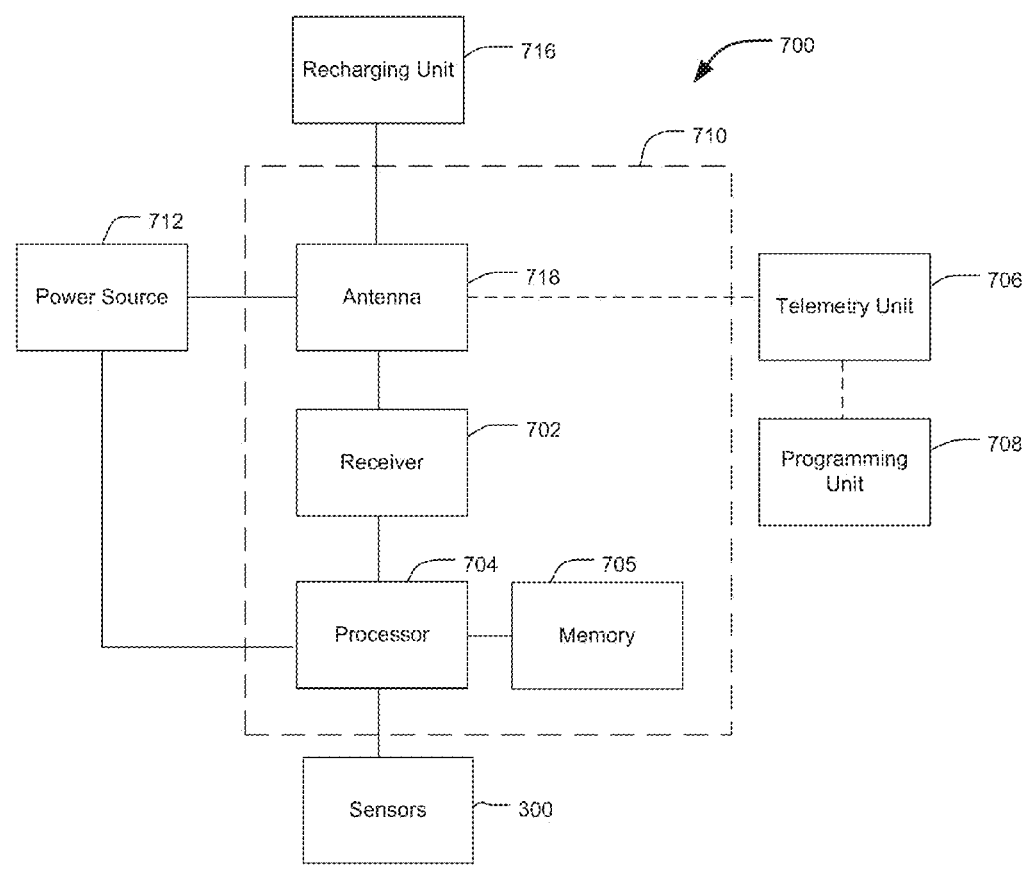
FIG. 7 is a schematic representation of a system for valve evaluation.

FIG. 7 is a schematic overview of one embodiment of the components of a valve diagnostic system 700 including an electronic subassembly 710 disposed within a control module. It will be understood that the valve diagnostic system can include more, fewer, or different components and can have a variety of different configurations.

Some of the components (for example, power source 712, antenna 718, receiver 702, and processor 704) of valve diagnostic system 700 can be positioned on one or more circuit boards or similar carriers. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like.

If the power source 712 is a rechargeable battery, the battery may be recharged using the optional antenna 718, if desired. Power can be provided to the battery for recharging by inductively coupling the battery through the antenna to a recharging unit 716 external to the user.

A processor 704 is included to obtain data from the sensors relating to force, pressure or elasticity measured by each of the sensors. Any processor can be used and can be as simple as an electronic device that, for example, is capable of receiving and interpreting instructions from an external programming unit 708 and performing calculations based on the various algorithms described above. A memory 705 may include data in the form of a dataset for performing various steps of the algorithm. For example, in some examples, data from sensors 300 relating to pressure, forces and the like may be passed to processor 704 and compared against a dataset stored in memory 705 to determine if further treatment and/or diagnosis is necessary. Additionally, data relating to valve diagnosis may be sent from programming unit 708 to processor 704 and the processor may determine the appropriate course of action or alert a clinician. Communication between programming unit 708 and processor 704 may be accomplished via communication of antenna 718 with telemetry unit 706. Additionally, sensors 300 may be in communication with one or more wearable devices to enable the user to continuously monitor or track the functionality of a therapeutic device. Such wearable devices may track or log data, and if necessary, provide the data to a clinician or alert emergency personnel if immediate attention is needed.

While the operation of sensor 300 has been described, it will be understood that other embodiments may be implemented in a similar manner, and that combinations of these embodiments may be possible. For example, any number of sensors 300 may be used and such sensors may be separable from the prosthetic replacement or repair device. It will also be noted that while the disclosures herein are predominately described in connection with the replacement of a tricuspid valve, the disclosures are equally applicable to the replacement of other valves, including a bicuspid valve, such as the mitral valve, as well as other implantable medical devices, such as annuloplasty rings and devices for taking general measurements of the vasculature for delivery of catheters. Additionally, in some variations, one or more of the sensors may be radiopaque to enable visualization during and/or after deployment. Sensors may also be in communication with a delivery system and/or other sensors to aid in placement, valve-in-valve or valve-in-ring procedures, or to function as locators or docking stations.

In some embodiments, a prosthetic device for implanting in a patient's heart includes a therapeutic device capable of restoring desired function to a native heart valve; and at least one sensor coupled to the therapeutic device and configured to monitor the function of the therapeutic device within the patient's heart, the sensor including a body, an induction coil disposed within the body and a capacitor in electrical communication with the inductor coil.

In some examples, the therapeutic device is a collapsible prosthetic heart valve including a stent having a proximal end and a distal end and a valve assembly disposed within the stent; and/or the stent includes an aortic section at the distal end of the stent, and the at least one sensor includes a plurality of sensors circumferentially disposed about the aortic section of the stent; and/or the stent includes a plurality of commissure features for coupling to the valve assembly, and the at least one sensor includes a plurality of sensors circumferentially disposed between adjacent ones of the plurality of commissure features; and/or the at least one sensor includes a plurality of sensors disposed on at least one of the proximal end or the distal end of the stent; and/or the at least one sensor is disposed on a lumenal surface of the stent; and/or the at least one sensor is disposed on an ablumenal surface of the stent; and/or the therapeutic device is a surgical valve including a frame having a plurality of posts, a ring-shaped cuff coupled to the frame, and tissue coupled to the plurality of posts to form a one-way valve, the at least one sensor being coupled to the ring-shaped cuff; and/or the therapeutic device is an annuloplasty ring and the at least one sensor is coupled to a lumenal surface of the annuloplasty ring.

In some embodiments, a method for diagnosing the functioning of a heart includes (a) introducing a prosthetic device into the heart, the prosthetic device including (i) a therapeutic device capable of restoring function to a native heart valve, and (ii) at least one sensor including a body, an inductor coil disposed within the body, and a capacitor in communication with the inductor coil, the at least one sensor being coupled to the therapeutic device; (b) acquiring cardiac measurements via the at least one sensor; and (c) determining the functioning of the heart based on the cardiac measurements.

In some examples, the therapeutic device is a collapsible prosthetic aortic heart valve including a stent, and a valve assembly disposed within the stent, and the step of acquiring the cardiac measurements includes collecting data related to aortic regurgitation; and/or the cardiac measurements are blood pressure measurements; and/or the cardiac measurements are blood flow measurements; and/or the method further includes coupling the at least one sensor to a memory and a processor, and calculating an aortic regurgitation index from the cardiac measurements using the processor; and/or the step of determining the functioning of the heart includes confirming proper functioning if the calculated aortic regurgitation index is greater than or equal to 25, and confirming improper functioning if the calculated aortic regurgitation index is less than 25; and/or the method further includes taking a corrective measure if the aortic regurgitation index is less than 25, and recalculating the aortic regurgitation index after the corrective measure is taken; and/or the corrective measure includes snaring the collapsible prosthetic aortic heart valve to readjust its position; and/or the corrective measure includes performing a valve-in-valve procedure.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A collapsible prosthetic device for implanting in a patient's heart, comprising:
   a stent having a plurality of struts, a proximal end, a distal end, a lumenal surface and an ablumenal surface;
   a valve assembly coupled to the stent, the valve assembly including a cuff and a plurality of leaflets, the cuff being disposed only over a portion of the stent so that the stent has an exposed portion in which neither the lumenal surface nor the ablumenal surface of the stent are covered by the cuff and a covered portion in which at least one of the lumenal surface or the ablumenal surface of the stent is covered by the cuff; and
   at least one sensor coupled to the exposed portion of the stent distal of the valve assembly such that the at least one sensor is spaced from the cuff and the plurality of leaflets, the at least one sensor being configured to monitor the function of a therapeutic device within the patient's heart, the sensor including a body, an induction coil disposed within the body and a capacitor in electrical communication with the induction coil.

2. The prosthetic device of claim 1, wherein the stent includes an aortic section at the distal end of the stent, and the at least one sensor includes a plurality of sensors circumferentially disposed about the aortic section of the stent.

3. The prosthetic device of claim 1, wherein the stent includes a plurality of commissure features for coupling to the valve assembly, and the at least one sensor includes a plurality of sensors circumferentially disposed between adjacent ones of the plurality of commissure features.

4. The prosthetic device of claim 1, wherein the at least one sensor includes a plurality of sensors disposed on at least one of the proximal end and the distal end of the stent.

5. The prosthetic device of claim 1, wherein the at least one sensor is disposed on the lumenal surface of the stent.

6. The prosthetic device of claim 1, wherein the at least one sensor is disposed on the ablumenal surface of the stent.

7. The prosthetic device of claim 1, wherein the body includes a protrusion formed from fused silica projecting inwardly toward an interior of the body, and the induction coil comprises a plurality of electrically conductive windings wrapped around the protrusion.

8. The prosthetic device of claim 7, wherein the plurality of electrically conductive windings defines a gap of between about 3 microns and about 35 microns between adjacent windings.

* * * * *